(12) United States Patent
Nyfors et al.

(10) Patent No.: US 6,466,035 B1
(45) Date of Patent: Oct. 15, 2002

(54) MICROWAVE FLUID SENSOR AND A METHOD FOR USING SAME

(75) Inventors: Ebbe Nyfors, Sandnes (NO); Årstein Bringsvor, Forus (NO)

(73) Assignee: Multi-Fluid ASA, Forus (NO)

( * ) Notice: Subject to any disclaimer, the term of this patent is extended or adjusted under 35 U.S.C. 154(b) by 0 days.

(21) Appl. No.: 09/701,185

(22) PCT Filed: Jun. 2, 1999

(86) PCT No.: PCT/NO99/00179
§ 371 (c)(1),
(2), (4) Date: Jan. 4, 2001

(87) PCT Pub. No.: WO99/63331
PCT Pub. Date: Dec. 9, 1999

(30) Foreign Application Priority Data

Jun. 3, 1998 (NO) ............................................... 982538

(51) Int. Cl.⁷ ............................................... G01R 27/32
(52) U.S. Cl. ........................ 324/634; 324/629; 324/640
(58) Field of Search ............................... 73/19.1, 61.44; 210/634; 324/324, 636, 640, 643, 629

(56) References Cited

U.S. PATENT DOCUMENTS

| | | | |
|---|---|---|---|
| 3,688,188 A | | 8/1972 | Bak et al. |
| 4,104,585 A | * | 8/1978 | Schofield ..................... 324/636 |
| 4,219,770 A | | 8/1980 | Weinert |
| 5,083,089 A | * | 1/1992 | Yukl .......................... 324/632 |
| 5,351,521 A | * | 10/1994 | Cracknell .................... 73/19.1 |
| 5,376,276 A | * | 12/1994 | Chung et al. ................ 210/634 |
| 5,389,883 A | | 2/1995 | Harper |
| 5,485,743 A | | 1/1996 | Taherian et al. |
| 5,754,055 A | | 5/1998 | McAdoo et al. |
| 5,926,024 A | * | 7/1999 | Blount et al. ................ 324/324 |

FOREIGN PATENT DOCUMENTS

WO    WO 93/21516    10/1993

* cited by examiner

*Primary Examiner*—Christine K. Oda
*Assistant Examiner*—Walter Benson
(74) *Attorney, Agent, or Firm*—Rothwell, Figg, Ernst & Manbeck

(57) ABSTRACT

A microwave sensor (3) for measuring the relative proportions of fluids is provided. The sensor (3) includes a tube (4) having a length (9) for accommodating the fluids flowing through said tube. The length (9) of the tube (4) makes up a part of the sensor (3). Also included are probes (6, 7) for transmitting electromagnetic energy into the sensor (3) and receiving electromagnetic energy from the sensor (3). The sensor (3) uses resonance at a resonant frequency ($f_m$) below the cut-off frequency ($f_m$) of the tube (4). The tube (4) includes at least one radially extending, conducting, internal fin (5) extending along the axis (10) of the tube (4). The fin (5) may be of regular or irregular shape and may be fixedly or detachedly arranged, e.g., through a slot (13).

8 Claims, 2 Drawing Sheets

MICROWAVE FLUID SENSOR AND A METHOD FOR USING SAME

The present invention relates to a meter for continuous measuring of the mixture proportions within fluids, e.g. measuring of the contents of water in oil or similar liquids flowing through a tube. The meter or sensor is simple and accordingly non-expensive to manufacture and well suited for measurements with simple electronics. The invention also relates to a method for undertaking such measurements.

Several meters for measuring of the water contents in oil are available on the market today. Some of these meters are based on the use of radioactive radiation, some of them are capacitive and some are based on use of microwaves.

Radioactive sensors are not acceptable or rather controversial in many environments due to the health hazard represented by the radiation, and the required security precautions. An sufficient accuracy also represents a problem as the radiation is most sensible for variations in density, and the difference in density between water and oil is rather low.

The capacitive meters detect the permittivity of the mixture of fluids at a frequency much lower than the frequency regularly used in sensors based upon microwaves. To explain the subject permittivity, it may e.g. be referred to ref. 1: Nyfors, E., P. Vainikainen, Industrian Microwave Sensors, Artech House 1989, chapt. 1. Such sensors are rather sensitive for different coatings as a large increase of the impedance will be the result of even a thin coating. The capacitive sensors also require a relatively complex design using a dielectric internal protection in the sensor to avoid direct contact between the electrodes and the fluid or the liquid which is to be measured.

The above problems are not involved with the microwave sensors.

Microwave sensors for measuring the contents of water in oil are conventionally based on a microwave resonator used as sensor. (Ref. chapt. 3 i the above book; ref. 1). To ensure that the sensor makes measurements of the complete flow, the resonator has to be a cavity resonator implemented in the tube. To ensure a sufficient quality factor (Q-factor) for the sensor, such a resonator must have a structure which prevents a leak of microwaves from the sensor and further out in the tube when the fluid flows. One possibility is to delimit a section of the tube physically by a net-like structure or screen in each end, with so narrow openings that the microwaves cannot radiate into the tube while the fluid may pass rather undisturbed. Each such end section then represents a short circuit for the microwaves. However, such a structure is very intrusive and represents a bar for cleaning and also for the flow if the flow includes solid particles. Such a cavity resonator has many different tuning modes with corresponding resonance frequencies. Accordingly a simple, self-oscillating electronic circuit may possibly not be used to determine the resonant frequency, as the risk to find an erroneous resonant frequency is large, in particular if the resonant frequency may vary within a broad range of frequencies. Accordingly a more complex measurement method has to be used, e.g. based on a VCO-circuit (=Voltage Controlled Oscillator) controlled by a personal computer (PC) in such a manner that the measuring signal is scanned over a certain range of frequencies.

An object of the present invention is to provide a meter based on a new microwave resonator having a simple structure, being less intrusive and less expensive than cavity resonators defined by net-like end sections. The new resonator is also well suited for measurements by a simple, self-oscillating electronic circuit, as it is possible to eliminate the two resonance frequencies closest to the desired frequency, so that the risk that the measurements are undertaken on an erroneous frequency are reduced or eliminated. Accordingly the invention has all the advantages of a microwave sensor, but is less intrusive than an conventional cavity resonator, is less expensive in production, and may use a simpler and less expensive electronic circuit.

The invention is in particular developed to measure the contents of water in oil, and then again especially for applications where the price is a delimiting factor and the requirements to the accuracy are not very high. Such an application may e.g. be measuring of the water contents in the fuel of a ship engine. According to one technique a small portion of water is added to the fuel in a ship's diesel engine to reduce the pollutant discharges of $NO_x$. One portion of the fuel will always be recirculated in a diesel engine and accordingly the fuel will already have a water contents when mixed with new fuel entering the system. To control the injection water the water contents accordingly must be measured. The requirements to the precision of these measurements are about ±2%, and the cost is very important. This invention is accordingly very well suited for such applications.

More generally the present invention may be used to measure the water contents in oil for all applications, and also the mutual proportions between two other fluids or liquids when only the continuous phase is non-conductive and the two fluids or liquids have different permittivities.

All of the above mentioned objects and advantages are met by using a method or a sensor according to the patent claims stated below.

In the following the present invention will be described in more detail by a thorough description of an embodiment which is an example. Here measuring of the water contents in oil is again used as an example. Similarly a cylindric sensor is used, also as an example. Accordingly this example does not exclude sensors having other cross sections than circular-sylindric. The sensor may e.g. have a polygonal or oval cross section without leaving the scope of the invention.

In the description it is referred to the following accompany figures:

FIG. 1 a principle drawing of a sylindric fin resonator (SFR-sensor), or more precisely a sylindric cavity resonator provided with an internal longitudinally at radially extending fin; illustrated by a cross section and a longitudinal section.

Figures 1A, 1B:
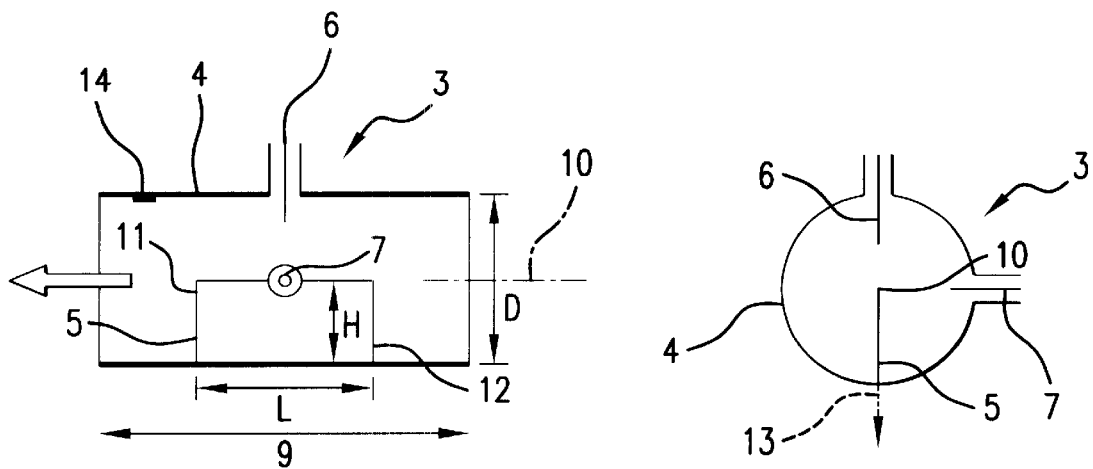

The same reference numerals are used in all the figures where applicable. However, the figures are simplified in such a manner that design details are not included when only representing a practical solution without a fundamental importance to the invention. And the scale in the drawings are not necessarily the same in all figures nor in different directions within each single figure, as the figures substantially are principle drawings made to give a good understanding of the invention.

In FIG. 1 the principle design of a sensor 3 according to the present invention is shown, by means of a longitudinal section and a cross section. The tube 4 is itself shown as a circular tube having an internal diameter D. Microwave probes 6,7 are fastened to the wall at the same longitudinal plane and perpendicular to each other.

Within the sensor is arranged a conducting fin 5 of height H and length L. The sensor 3 extends in the practical solution somewhat further out than the fin 5, on the figure assumed by the length 9. The exact length 9 of the total sensor may be difficult to define as the electromagnetic field extends further out than the fin, e.g. 10% outside the fin, depending of the exact design of the fin. In a practical solution the sensor may have the same length L as the fin 5. When the sensor is installed a portion of the adjacent tube will act as a part of the sensor itself, as the electromagnetic field will extend into a portion of the tube. Accordingly the sensor may be designed with a length 9 corresponding to the length of the fin 5, and the length of the fin may in turn correspond approximately to the diameter D of the tube 4.

The present invention is characterized by measuring of the permittivity of a fluid mixture comprising two components, and from this to calculate the relative proportions between the two components by use of a calibrated model, as a sylindric fin resonator (SFR) is used as a sensor. Previously the resonant frequency is detected whereupon the permittivity is calculated and during this process e.g. a positive-feedback connected and self-oscillating amplifier is used (the TSF-method). The amplifier included in the electronic circuit may preferably be of such a type that the amplification may be adjusted, e.g. by changing the voltage of the amplifier, so that a large dynamic range is obtained for the resonant curve for the sensor.

When two fluids A and B, e.g. liquids having different permittivity $\epsilon_{rA}$ and $\epsilon_{rB}$ repectively, are mixed, the permittivity of the mixture ($\epsilon_{rm}$) will depend of the relative proportions $\phi$ of the two fluids, ref. e.g. ref. 1, chapt. 2. The proportional relation is normally expressed as the relative volume of one of the components compared to the total volume of the mixture, e.g.

$$\phi_A = \frac{V_A}{V_A + V_B} \tag{1}$$

where $V_A$ is the volume of the fluid A and $V_B$ is the volume of fluid B in a sample of the mixture having the volume $V_m = V_A + V_B$. If the fluid A e.g. is water while the fluid B is oil, the expression $\phi_A$ represents the water contents of the mixture. How the permittivity $\epsilon_{rm}$ of the mixture depends of the proportional relation $\phi$, also depends of how the fluids in question will mix, and accordingly is a specific value depending of the two fluids. As a model for this dependency $\epsilon_{rm}(\phi)$ either a previously known model known from ref. 1, chapt. 2.4, or an empiric, calibrated model may be used. The value of $\phi$ may then later on be calculated from a measured value of $\epsilon_{rm}$ by use of this model.

To find $\epsilon_{rm}$ a microwave resonator may be used as sensor. Such a sensor has a resonant frequency dependent of the permittivity of the mixture within the sensor. If the resonant frequency is $f_0$ when the sensor is empty and $f_m$ when it is filled up with said mixture, the result will according to ref. 1, page 133 be:

$$\varepsilon_{rm} = \left(\frac{f_0}{f_m}\right)^2 \tag{2}$$

From ref. 2: Finish patent FI 69372 it is previously known to build a microwave resonator in a tube by using such a structure that the resonant frequency is below the cut off frequency, see also ref. 1, page 11, for the wave mode in said tube, see also ref. 3: Collin, R. E., Foundations for Microwave Engineering, McGraw-Hill, 1966, chapt. 3. The microwaves then cannot travel through the tube and accordingly they will not extend further out in the tube from the sensor. Accordingly the resonator does not need any screening in shape of nets or similar end pieces to obtain a high Q-factor. The present invention, a resonator having an internal radial fin (SFR-sensor), represents a new method for designing such a microwave resonant sensor.

Within a sylindric wave conductor, with other words a circular electric contacting tube, the microwaves may travel according to different wave mode which may be referred to as $TE_{nm}$ or $TM_{nm}$, see ref. 3, chapt. 3, each having its specific cut-off frequency f. being dependent of the internal radius $\alpha$ of the tube:

$$f_{c,nm} = \frac{cp_{nm}}{2\pi\alpha}, (TM_{nm}) \tag{3}$$

$$f_{c,nm} = \frac{cp'_{nm}}{2\pi\alpha}, (TE_{nm}) \tag{4}$$

where c is the light velocity in vacuum ($3 \times 10^8$ m/s), $p_{nm}$ is zero-crossing number m for the Bessel function of first type and degree n, $p'_{nm}$ is zero-crossing number m for the derived value of the Bessel function of first type and degree n.

Table I shows the values of $p_{nm}$ and $p'_{nm}$ for a conventional cylindric wave guide.

The equations (3) and (4) are also valid for a wave guide shaped as a sector of a cylinder. If the sensor angle is 360° the wave guide looks like a cylinder with a radial internal fin extending from the wall and into the central line of the tube, and fastened to the tube. Table II shows the values of $p_{nm}$ and $P'_{nm}$ for such a fin wave guide or wave conductor.

TABLE I $p_{nm}$ and $p'_{nm}$ for the wave modes having the lowest cut-off frequencies in a sylindric wave guide.

| | TM | | | TE | | |
|---|---|---|---|---|---|---|
| n | $p_{n1}$ | $p_{n2}$ | $p_{n3}$ | $p'_{n1}$ | $p'_{n2}$ | $p'_{n3}$ |
| 0 | 2,405 | 5,520 | 8,654 | 3,832 | 7,016 | 10,174 |
| 1 | 3,832 | 7,016 | 10,174 | 1,841 | 5,331 | 8,536 |
| 2 | 5,135 | 8,417 | 11,620 | 3,054 | 6,706 | 9,970 |

Table II: $P_{nm}$ and $p'_{nm}$ for wave modes having the lowest cut-off frequencies in a wave guide with fin according to the present invention.

TABLE II $p_{nm}$ and $p'_{nm}$ for the wave modes having the lowest cut-off frequencies in a wave guide with fin according to the present invention.

| | TM | | | TE | | |
|---|---|---|---|---|---|---|
| n | $p_{n1}$ | $p_{n2}$ | $p_{n3}$ | $p'_{n1}$ | $p'_{n2}$ | $p'_{n3}$ |
| ½ | π | 2π | 3π | 1,1656 | 4,604 | 7,709 |
| 1 | 3,832 | 7,016 | 10,174 | 1,841 | 5,331 | 8,536 |
| 2 | 5,135 | 8,417 | 11,620 | 3,054 | 6,706 | 9,970 |

From equations (3) and (4) one can find that the limit or cut-off frequency for a wave mode is direct proportional to $p_{nm}$ or $p'_{nm}$. From table I it is found that the mode with the lowest cut-off frequency in a cylindric wave guide will be $TE_{11}$ with $P'_{11}=1.841$ and from table II it is seen that the lowest possible mode within a fin wave guide is $TE_{1/2}1$ with $p'_{1/2}1=1.1656$. Accordingly the lowermost cut-off frequency in a fin wave guide is 37% below that in a sylindric wave guide; or with other words if a fin is connected to the wall in a sylindric wave guide, waves with a frequency 37% lower than the previously minimum frequency may propagate in the part of the wave guide being equipped with such a fin.

A microwave resonant mode is based on a $TE_{nm}$ or a $TM_{nm}$ wavemode. The resonator comprises a length L of the wave guide terminated by short-circuited or open end sections, so that the present mode is reflected and accordingly produces a standing wave in the defined part of the wave guide. The wave mode then obtains a third index 1 associated with the length L of the resonator. The resonant frequency for the different modes then will be; see also ref. 1, page 150:

$$f_{r,nml} = \frac{c}{2}\left[\left(\frac{x_{nm}}{\pi a}\right)^2 + \left(\frac{1}{L}\right)^2\right]^{1/2} \quad (5)$$

where $x_m$ may have the value of $p_{nm}$ or $p'_{nm}$.

Within a resonator having short-circuited end sections resonant TM-modes with indexes $1=0,1,2,\ldots$ and a resonant TE-mode with index $1=1,2,3,\ldots$ may be obtained. If the end sections are open, resonant TM-modes having indexes $1=1, 2,3,\ldots$ and TE-modes with indexes $1=0,1,2,\ldots$ may appear. All the resonant modes with an index $1=0$ have a resonant frequency independent of the length L of the resonator and identical with the cut-off frequency for the wave mode.

If a fin 5 of length L is fastened to the wall in a cylindric tube 4 so that the tube 4 will extend beyond the fin 5 in both ends, a resonator with open ends is obtained. The lowermost resonant mode then will be $TE_{1/2}10$ ($p'_{nm}=1.1656$) with a resonant frequency independent of L and identical with the cut-off frequency for the wave mode $TE_{1/2}1$, being below the lowermost cut-off frequency of the tube 4 beyond the fin 5, $TE_{11}$ ($p'_{nm}=1.841$). Therefore the microwaves cannot travel further out in the tube and the mode $TE_{1/2}10$ accordingly has a high Q-factor. In a practical embodiment the electromagnetic field close to the open ends of the fin 5 will be disturbed in such a manner that the measured resonant frequency will be approximately 5% higher than the theoretically calculated value. However, this difference is so small that it has no consequences for the above explanation which is based on the theoretical resonant frequencies. This is obtained with a cylindric fin resonator SFR which is an example of the present invention and which may be used to determine the permittivity of the mixture flowing in the tube. The structure is very simple and less intrusive than in corresponding sensors having short-cirvuited ends.

Figure 2:
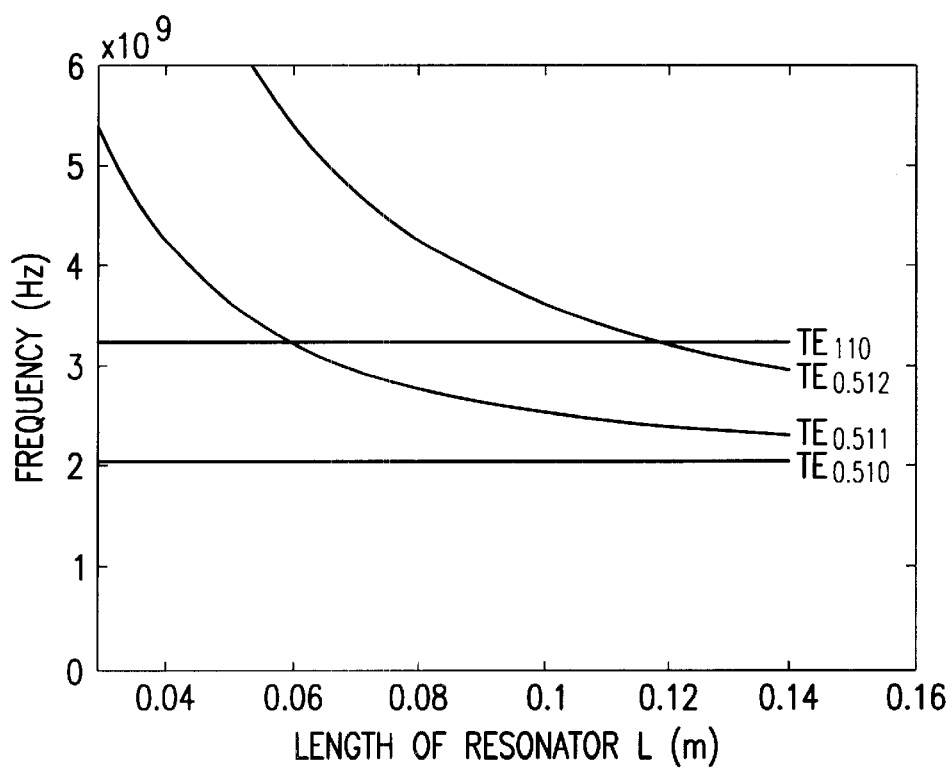
FIG. 2 shows the theoretic frequency of the four resonance modes with as low a frequency as possible in an SFR-sensor as a function of the fin length. The internal diameter of the tube is 54 mm.

In addition to $TE_{1/2}10$ the lowest possible resonant modes in an SFR-sensor will be $TE_{1/2}11$, $TE_{1/2}12$ and $TE_{110}$. Among these values the resonant frequencies for $TE_{1/2}11$ and $TE_{1/2}12$ will depend of L. In FIG. 2 the calculated resonant frequencies (according to equation (3)) are shown for those four modes. According to FIG. 2 the frequency distance between the resonant frequencies for $TE_{1/2}10$ and $TE_{1/2}12$ will be large when the length of the resonator or the fin 5 (L) is short, e.g. equal to the internal diameter D of the tube 4.

Figure 3B:
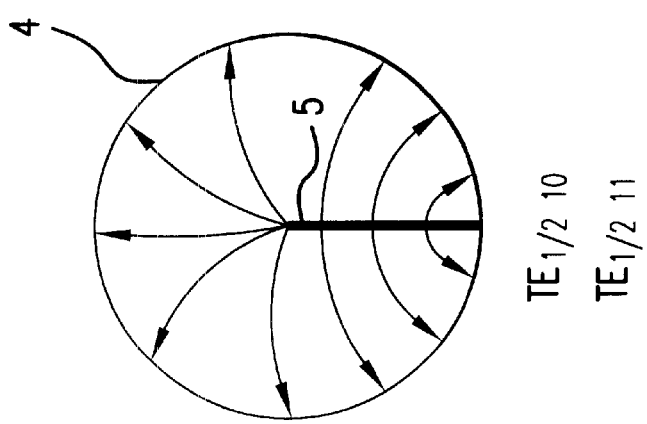
FIG. 3 shows the electrical field for the resonance modes $TE_{110}$, $TE_{1/2}10$ and $TE_{1/2}11$ in an SFR-sensor.
Figure 3A:
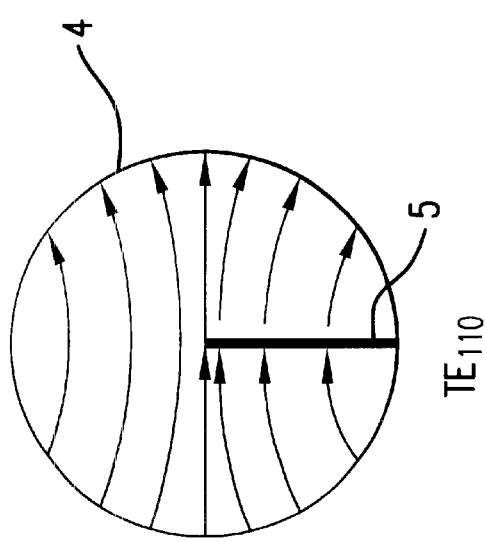

In FIG. 3 the electrical field of resonant mode $TE_{1/2}10$, $TE_{1/2}11$ and $TE_{110}$ for a SFR-sensor is shown. The mode $TE_{110}$ has an electrical field which is zero close to the wall of the tube opposite to the fin 5. If the cables 2 of the metering circuit (see FIG. 4) is connected to the sensor 3 via probes 6 and 7 which are coupled to the electrical field being perpendicular to the wall of the tube 4 of the sensor 3 so that one of the probes 6 opposes the fin 5; all coupling to the mode $TE_{110}$ is avoided.

The mode $TE_{1/2}11$ has such a field picture in the longitudinal direction of the tube that the field maximum occurs at the end of the fin 5 while the field strength is zero at the middle of the fin 5. This will be the case for all resonant modes having an index $1=1$; see also ref. 1, page 314; when the ends of the resonator are open. If the probes 6,7 then are arranged so that the distance to both of the ends 11,12 of the fin is equal, such as shown in FIG. 1, coupling is also avoided to mode $TE_{1/2}11$. As mode $TE_{1/2}10$ in a SFR-sensor is used for measuring of the permittivity of the fluid mixture which is to be measured, there will be large distance to next mode due to the fact that when the probes 6,7 are connected as shown in FIG. 1, coupling to the modes $TE_{1/2}11$ and $TE_{110}$, are avoided. Accordingly the SFR-sensor shown in FIG. 1 is in particular well suited for measuring using TSF-electronics, because the risk that the electronics shall tune to an erroneous resonant frequency easily may be avoided by choosing a correct frequency response of the amplifier (i.e. the amplification as a function of the frequency).

Figure 4:
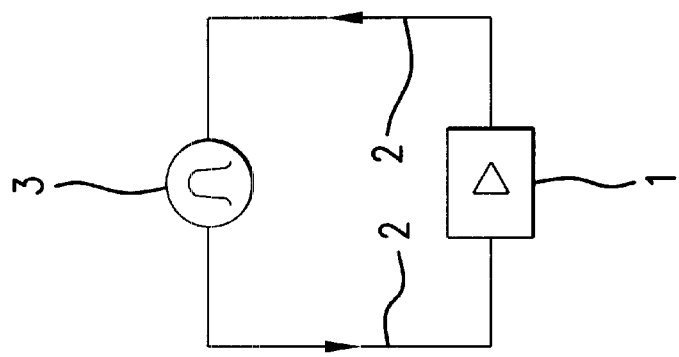
FIG. 4 illustrates the principle of the TSF-method (feedback connected self-oscillating amplifier), used for metering of the resonant frequency.

The principle of the TSF-method for measuring the resonant frequency of a sensor, is shown in FIG. 4, and is also more thoroughly described in ref. 1: chapt. 3.4.3, and in ref. 4: "Vainikainen, P. V., Measurement Electronics of Industrial Microwave Resonator Sensors, Thesis for the degree of Doctor of Technology, Helsinki University of Technology, Radio Laboratory, Report S 194, 1991". The measurement is based on an amplifier 1 which is feedback connected by means of cables 2 and the sensor 3. If the amplification in the amplifier 1 at a certain frequency is above the total attenuation in the cables 2 and in the sensor 3, the net positive amplification (expressed in dB) and the signal will be amplified for each new reound through the circuit. Accordingly the circuit will start oscillating at this frequency. The sensor 3 which acts as a band pass filter and therefore this situation will in a practical solution only occur at the resonant frequencies and very close to these. If amplifiers having an amplification being inversely proportional to the frequency are used, oscillations are only possible at the lowermost resonant frequency. This applies in particular to a SFR-sensor having a large frequency distance to the next resonant frequency, also if the coupling to this is stronger than that to the lowermost mode.

In addition to the requirement that the net value of the application must be positive, the phase shift in the circuit also must have such a value that the signal obtains identical phase after each round, to maintain the oscillation. At a certain oscillation frequency the total phase shift accordingly will be:

$$\Delta\phi = n \cdot 360° \quad (6)$$

where n is an integer. This means that the oscillation usually do not occur exactly at the resonant frequency, but on the closest frequency at which n is an integer and the net amplification is positive. If the resonant frequency is changed as a result of a change in the proportions of the mixture to be measured and accordingly of the permittivity, the oscillation frequency will only change stepwise so that n always will be an integer. This will give a certain loss of accuracy in the measurement.

During one round in the TSF-circuit, the phase of the signal passing the sensor the amplifier and the cables, will be shifted. The phase shifting in the amplifier may be considered as an additional cable length, and just at the resonant frequency the phase shift in the sensor is zero. The phase requirement then leads to that the total length d of the cables, included the effective increasement of the length caused by the amplifier, must be an integer multiplied with the wave length in the cables. The distance between frequencies at which oscillations are possible then will be $$\Delta f = \frac{(n+1)c}{d\sqrt{\varepsilon_{rc}}} - \frac{n \cdot c}{d\sqrt{\varepsilon_{rc}}} = \frac{c}{d\sqrt{\varepsilon_{rc}}} \qquad (7)$$

where $\epsilon_{rc}$ is the permittivity for the insulation material of the cables. If e.g. d=20 m and $\epsilon_{rc}$=2.2, then $\Delta f$=10.1 MHz. The sensitivity for an SFR-sensor 3 having an internal diameter D of 54 mm, and a length L of the fin 5 like 50 mm, has been found to have a mean value approx. 15 MHZ/$\%_{water}$. The inaccuracy caused by this phase requirement will then be $$\Delta\%_{water} = \pm \frac{0,5 \cdot 10,1 \text{ MHz}}{15 \text{ MHz}/\%_{water}} = \pm 0,34 \ \%_{water} \qquad (8)$$

In addition to the resonant frequency the phase shift in the sensor will contribute so that the inaccuracy in pracis will be a little below the value calculated according to equation (7). This result depends on the width of the resonant function, but will be approx. 10%, so that the final result of equation (8) will be ±0.31% water.

When the length of cable d is chosen, the width of the resonance function also has to be taken into account so that the distance between the frequencies where the phase shift requirements are met, not will be too large. An acceptable requirement is in practise that $\Delta f$ in equation (7) has to be less than the width on half power level $\Delta f_{3db}$ on the resonance function, see also ref. 1, page 136. Oscillation will then always be possible if the net amplification at the resonant frequency is above 3 dB. During a measuring situation then $$\Delta f < \Delta f_{3dB} = \frac{f_m}{Q} \qquad (9)$$

where Q is the quality factor of the resonance. Q is dependent of the measured permittivity of the mixture, and how strong the coupling between the probes 6 and 7 and the circuit with the sensor 3 are, see also ref. 1, pages 140 and 146. The coupling may be adjusted by an empiric adjustment of the length of the probes. For the above mentioned SFR-sensor the measured Q-value varied from 117 to 39, while the contents of water in oil varied from 0% to 40% and the coupling of the resonant frequency at 0% then was −8 dB.

The total attenuation in the circuit is a sum of the attenuation in the cables 2, in the sensor 3 and the attenuators which in practical solutions always are required to enhance the impedance adaption in such measuring systems. The attenuation in the sensor 3 varies with the attenuation of the mixture which is to be measured.

To ensure that the amplification in the circuit always will be positive, the amplifier 1 will i practice comprise two or several amplifier steps connected in series. When the TSF-electronics starts oscillating, the last of the steps in the amplifier will reach saturation and send out the signal comprising many harmonic components. Intermodulation in the last amplifier step then will damage the signal. This may be avoided by regulation of the amplification, e.g. by regulating the voltage to the amplifier.

According to the present invention an auxiliary equipment, e.g. a computer is used to regulate the amplification while the signal in the circuit is measured. The amplification is increased, and when the oscillations starts the frequency of the signal is measured in a manner known per se. This results in a very broad dynamic range for the meter, which accordingly accept large variations in the attenuation of microwaves in the mixture to be measured.

An electronic TSF-circuit has been designed and tested in which three amplifiers of the type MSA-0885 produced by Hewlett-Packard are connected in series. The voltage to the first and last amplifier step is controlled by a computer. The attenuators in the circuit represent together −18 dB, and the TSF-electronics is connected to the above mentioned SFR-sensor, such that d=20 m. This meter has been used in a test where the water contents in oil from the Statfjord field were measured. The tolerance for this meter was better than +0,4%$_{water}$. This corresponds reasonably with the number ±0,31%$_{water}$ as uncertainties in the calibration of the model have to be taken into account for $\epsilon_{rm}(\phi_{water})$. is The details of this solution may vary in many manners within the scope of the present invention. The cross section of the tube and the resonators may be modified in countless different ways as not only circular sylindric cross sections may be used for the sensor, but also polygon 21, oval and irregular shapes, if possible adapted to the cross section of the tube itself. The shape, location and the ends 11,12 of the fin 5 may also be modified. The fin may e.g. be perforated or equipped with holes, and may e.g. have a grid or net structure. It may be rectangular as assumed on FIG. 1, but it may also have a more irregular and profilated shape, not shown separately on the drawings. As an example it may shaped as a semi circular plane. In a similar manner one or both end portions 11,12 of the fin may be round or tilted to give a less abrupt end. The thickness of the fin 5 is not mentioned in particular, as it is a non-critical value, however, it will normally be made as thin as possible without being detrimental to the structural strength of the construction. The fin may also be split into several fin segments which may have the shape of closely arranged segments having equal or different length. In this situation it may talked about several fins or sub-fins with an effective total length measured longitudinally to the tube, while each sub-fin may be rather short. Similarly each fin or sub-fin may have a moveout when the exact location along a radial plane is considered, as a certain distance from this radial plane also may be accepted.

Due to practical considerations the fin 5 or the fins may be arranged within a slot 13 in the wall of the tube 4 or sensor so that it (they) may be pulled out sidewise of the tube to be changed, cleaned or for maintenance. This is an alternative even if the preferred embodiment will be a fix and stabil construction without such simple possibilities for this assembling or re-shaping. The fin may also be resilient, e.g. by being suspended in a springy way so that an internal load, e.g. caused by particles in the fluid flow, at certain intervals may force the fin more or less out through the mounting slot and into a sealed slider, while the fin thereafter again will spring back into the sensor.

Other modifications may be change of the material in the sensor which may be selected among all known materials for wave guides and cavity resonators. The probes may also be designed in many different ways, but will normally have a coaxial shape with conventional terminals while the length of the probe may be changed as explained above. The number of the probes and the location of same may also vary as the desired frequency response is taken into consideration.

Even when a sensor with a radially extending fin is used, it is not necessary to use only the method described to obtain resonance. Resonance may be obtained or the resonant frequency may also be determined according to different and possibly conventional methods, however, the method described is deemed to be a preferred method. This is also the case for using of a feedback connected amplifier, which also only represents a preferred method, as it represents an elegant and non expensive solution. However, the present invention also covers a fin resonator used together with other external systems to determine the resonant frequency, as the varied use of at least one fin within the resonator to obtain a resonant frequency below the cut-off frequency of the tube is in itself a new and inventive solution no matter which measuring method that is being used.

Accordingly the use of the invention may also be more than measuring the water contents in oil. The invention may be used to determine the proportional relations between two random fluids such as gases, liquids or mixtures of gases and liquids.

Nor are self oscillating electronic circuits and adjustable gain quite necessary requirements to obtain measurements with such a fin resonator, but such remidies are thought to be advantageous as they give a large measuring range and represent a very inexpensive solution.

The method may also be varied in many manners. An important matter is that the sensor may be used for measuring of the permittivity and the conductivity at the same time. In a practical solution this may be done as the probes 6,7 also are used to measure the conductivity of the mixture when passing. This will in particular be valuable when the continuous phase of the mixture is electrically conducting, which again will be the case when the continuous phase is water including salt or oil. Electronic circuits may then be connected to measure the conductivity in parallel with the circuits to measure the permittivity. Accordingly one single equipment may be used to measure both the permittivity and the conductivity, and accordingly the measuring range for water in oil will be expanded to cover the complete range from 0% water to 100% water. However, this does not omit the possibility of only measuring the permittivity or only the conductivity. Measuring of the permittivity is best suited when the mixture is non-conducting, while the conductivity measurements are well suited when the mixture is conductive. Accordingly the measuring methods supplements each other.

When the conductivity is measured, it may also be of use to measure the temperature of the mixture as the temperature affects the exact value of the conductivity. Such a temperature measurement may be undertaken by a specific detector 14 as assumed on FIG. 1.

What is claimed is:

1. A microwave sensor (3) for measuring the relative proportions of fluids, comprising:
   a tube (4) having a length (9) for accommodating said fluids flowing through said tube; and
   probes (6, 7) operable to transmit electromagnetic energy into the sensor (3) and receive electromagnetic energy from the sensor (3), said sensor (3) using resonance at a resonant frequency ($f_m$) below the cut-off frequency ($f_m$) of the tube (4), wherein the tube (4) comprises at least one radially extending, conducting, internal fin (5) extending along the axis (10) of said tube (4).

2. A microwave sensor as claimed in claim 1, characterized in that the fin(s) (5) stretch(es) radially along the sensor from the internal wall of the tube (4) to or towards the central axis (10) of said tube.

3. A microwave sensor as claimed in claim 1, characterized in that the height (H) of the fin(s) (5) in radial direction varies over at least one portion of the fin's length (L), and that the total length (L) of the fin(s) is approx. equal to the internal diameter (D) of the tube (4).

4. A microwave sensor as stated in claim 1, characterized in that a first probe (6) is located centrally to the fin's (5) (the fins') total length (L) and is connected to the tube (4) diametrally to the fin(s) (5), while the other probe (7) is arranged perpendiculary to the plane in which the fin(s) (5) and the first probe (6) are situated.

5. A microwave sensor as stated in claim 1, characterized in that the fin(s) (5) is(are) mounted within a longitudinal slot (13) in the sensor wall so that it (they) may be taken out through said slot for change/cleaning/maintenance, possibly against a mechanical bias.

6. A method for measuring the relative proportions (4)) between two fluids (A, B) situated within a tube (4) of a sensor (3), said tube (4) comprising at least one radially extending, conducting internal fin (5) extending along an axis (10) of said tube (4), a first probe (6) for transmitting microwave energy and a second probe (7) for receiving microwave energy, said measuring being performed while the sensor(3) is resonant, comprising the steps of:
   determining the resonant frequency (fm);
   calculating the permittivity ($\epsilon_{rm}$) from said resonant frequency;
   comparing the permittivity ($\epsilon_{rm}$) to the permittivity of a known, empirically, calibrated model comprising the same fluids (A, B); and
   determining the relative proportions (φ) from the comparison,
   wherein a positive feedback connected amplifier (1) having a frequency dependent amplification is used for measuring the resonant frequency, as the amplification, at least at the resonant frequency used, is above the attenuation in a feedback loop (1, 2, 3), but otherwise below the attenuation in said feedback loop, and
   a phase shift (Δφ) in the feedback loop (1, 2, 3) is derived from a formula:

$$\Delta\phi = n360°,$$

where n is an integer above or equal to 1.

7. A method according to claim 6, characterized in that the amplifier (1) comprises at least two series connected amplifier units.

8. A method according to claim 7, characterized in that the amplification in the feedback loop (1, 2, 3) is adjusted from a low value until self-oscillations occur and the frequency of said oscillations is measured during the oscillation process, such that the amplification is inversely proportional to the frequency thereby ensuring that the lowermost resonant frequency present is used during the measurement.

* * * * *